United States Patent [19]

Krüger

[11] 4,289,897
[45] Sep. 15, 1981

[54] METHOD FOR PRODUCTION OF ACYLHYDRAZONES OF FORMYL-ACETIC ACID ESTER

[75] Inventor: Hans-Rudolf Krüger, Berlin, Fed. Rep. of Germany

[73] Assignee: Schering Aktiengesellschaft, Berlin and Bergkamen, Fed. Rep. of Germany

[21] Appl. No.: 196,150

[22] Filed: Oct. 10, 1980

[30] Foreign Application Priority Data

Nov. 7, 1979 [DE] Fed. Rep. of Germany ....... 2945406

[51] Int. Cl.³ .................. C07C 133/04; C07C 133/00
[52] U.S. Cl. ...................................... 560/159; 560/168
[58] Field of Search ...................... 560/159, 168, 169

[56] References Cited

U.S. PATENT DOCUMENTS 3,886,211  5/1975  Keenan ............................. 560/168
4,236,017  11/1980  Boschi ............................. 560/159

*Primary Examiner*—Natalie Trousof
*Assistant Examiner*—Michael Shippen
*Attorney, Agent, or Firm*—Michael J. Striker

[57] ABSTRACT

A process is provided for production of acylhydrazones of formyl-acetic acid ester of the general formula

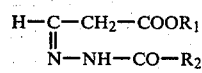

wherein $R_1$ is an alkyl group with from 1 to 6 carbon atoms and $R_2$ is an alkoxy group or an amino group. A propiolic acid ester of the general formula

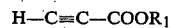

is contacted with hydrazine derivatives of the general formula

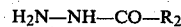

in the presence of a solvent such as water or a lower alcohol. The resulting products are technically valuable starting materials for the production of biocides, for example of 1,2,3-thiadiazole derivatives.

10 Claims, No Drawings

METHOD FOR PRODUCTION OF ACYLHYDRAZONES OF FORMYL-ACETIC ACID ESTER

DESCRIPTION

BACKGROUND OF THE INVENTION

1. Field of the Invention

This invention relates to a process for the production of acylhydrazones of the formyl-acetic acid ester, which are suitable as starting materials for the preparation of 1,2,3-thiadiazole derivatives.

2. Brief Description of the Background of the Invention Including Prior Art

Formyl-acetic acid ethyl ester semicarbazone (W. Wislicenus, H. W. Bywaters, Liebigs Annalen der Chemie Vol. 356, page 50 [1907]) and formyl-acetic acid ethyl ester-ethoxycarbonylhydrazone (R. Raap, R. G. Micetich, *Canadian Journal of Chemistry*, Vol. 46, page 1057 [1968]) are already known from the literature. Both compounds are produced by a process wherein the sodium salt of the formyl-acetic acid ester is reacted with corresponding hydrazine derivatives.

A precondition of this process is the synthesis and isolation of the formyl-acetic acid ester sodium salt. This can however only be produced via complicated and extended work processes in unsatisfactory yields (German Pat. No. 708,513; Great Britain Pat. No. 568,512; U.S.P. 2,394,255, W. Deuschel, Helv. Chim. Acta vol. 35, page 1587 [1952]).

One process (L. Beer and P. Halbig, German Pat. No. 708,513) condenses formic acid ester and acetic acid ester with sodium alcoholate in an autoclave reaction, wherein the acetic acid ester is produced from the excess alcohol by pressurizing with carbon monoxide.

This process is unsuitable for an economic technical production in view of the poor yields and of the equipment expenditures for the pressure reaction. The yields listed in the literature cannot be reproduced.

In another process (E. H. Northey, Great Britain Pat. No. 568,512; U.S. Pat. No. 2,394,255) acetic acid ester and formic acid ester are condensed with alcoholfree sodium alcoholate by employing carbon monoxide under pressure. Again this process is unsuitable for industrial production based on the required autoclave reaction and the insufficient yields.

A third process (W. Deuscherl, Helv. Chim. Acta vol. 35, page 1587 [1952]) condenses a mixture of acetic acid ester and formic acid ester with alcoholfree sodium alcoholate produced from powderized sodium and alcohol in ether. Based on the employment of suspensions of sodium in ether and in view of the poor yields, this process is at best limited to laboratory work, but is completely unsuitable for a technical production.

SUMMARY OF THE INVENTION

1. Purposes of the Invention

It is an object of the present invention to provide a process for unproblematical production of acylhydrazones of formyl-acetic acid ester in a one step reaction.

It is another object of the present invention to provide a process for the production of acylhydrazones of formyl-acetic acid ester avoiding the use of the intermediary formyl-acetic acid ester sodium salt.

It is a further object of the present invention to provide a process for the production of acylhydrazones of formyl-acetic acid ester, which is technically simple, provides high yields and is suitable for industrial production of this class of materials.

These and other objects and advantages of the present invention will become evident from the description which follows.

2. Brief Description of the Invention

The present invention provides a process for the production of acylhydrazones of formyl-acetic acid ester of the general formula

wherein $R_1$ is an alkyl group with from 1 to 6 carbon atoms and $R_2$ is an alkoxy group or an amino group comprising contacting a propiolic acid ester of the general formula

with hydrazine derivatives of the general formula

in the presence of a solvent.

The solvent can be a member of the group consisting of water, organic solvents and mixtures thereof. Preferred solvents are alcohols having from 1 to 4 carbon atoms and mixtures of water and alcohols having from 1 to 4 carbon atoms in a weight ratio of from about 2:1 to 1:2.

The contacting can occur at temperatures of from about $-20°$ C. to $+100°$ C. and preferably occurs at temperatures of from about $0°$ C. to $50°$ C. A preferred propiolic acid ester is propiolic acid ethyl ester and preferred hydrazine derivatives include semicarbazide and hydrazinoformic acid ethyl ester.

The invention accordingly consists in the process hereinafter described in detail and of which the scope of application will be indicated in the appended claims.

DESCRIPTION OF INVENTION AND PREFERRED EMBODIMENTS

In accordance with the present invention there is provided a process for the production of acylhydrazones of the formyl-acetic acid ester of the general formula

wherein $R_1$ is an alkyl group with from 1 to 6 carbon atoms and $R_2$ is an alkoxy group, preferably an alkoxy group having from 1 to 4 carbon atoms, or an amino group and which is characterized in that a propiolic acid ester of the general formula

is reacted with hydrazine derivatives of the general formula

in an aqueous medium, in organic solvents or in a mixture of water and organic solvents.

The process of the present invention employs starting materials which are easily accessible and allows a technically simple and not dangerous production of the desired products in high yields.

The synthesis of the acylhydrazones of the formula (I) is performed starting with propiolic acid esters of the formula (II) by reaction with about equimolecular amounts of hydrazine derivatives of formula (III) in an aqueous solution, in organic solvents or in a mixture of water with organic solvents and preferably in an aqueous and/or alcoholic medium. It is advantageous to add the propiolic acid ester in portions or together with a solvent such as an alcohol having from 1 to 4 carbon atoms to a thinned solution of the hydrazine component in water and/or an alcohol having from 1 to 4 carbon atoms. The weight ratio of alcohol to water in the mixture can vary over a wide range as water alone or alcohol alone can also be employed. Preferably the weight ratio of alcohol to water can be 1:1. The addition of the reactants can also be performed in reversed sequence. The reaction occurs at temperatures from about $-20°$ C. to 100° C. and a preferred temperature range is from about 0° C. to 50° C.

Examples for alcohols having from 1 to 4 carbon atoms include methanol, ethanol, propanol, isopropanol, butanol, sec.-butanol, tert.-butanol.

After the reaction has been performed the usually solid reaction products can be isolated by filtration, by freezing them out or by removal of the solvent in the shape of colorless crystals.

They can be easily recrystallized from suitable organic solvents such as ketones, alcohols, nitriles, esters, ethers and chlorinated hydrocarbons such as acetone, methanol, ethanol, acetonitrile, acetic acid ester, di-isopropylether and chloroform and are stable at room temperature. In general, the compounds are obtained in such a high degree of purity that they can be further reacted after recrystallization.

The following examples are provided to illustrate the process of the present invention.

EXAMPLE 1

Production of Formyl-acetic acid ethyl ester-semicarbazone (3-Semicarbazono-propionic acid ethyl ester)

11.15 g (0.1 mole) semicarbazide hydrochloride are dissolved in 10 ml water in a three neck 100 ml round flask with stirrer and thermometer and 10.0 g (0.1 mole) potassium hydrogen carbonate are added and then 10 ml ethanol are employed to thin. To this during 5 minutes are added drop by drop 9.8 g (0.1 mole) propiolic acid ethyl ester. The reaction temperature is kept for 4 hours at about 30° C. and a thick crystal paste forms slowly. After standing over night the product is cooled down in an ice bath and thinned with 10 ml water. The crystals are sucked off, are washed with 10 ml water and dried in vacuo at 40° C. to constant weight.

Yield: 16.2 g=93.5 percent of theory
Fp. 147°–148° C.

Thin layer chromatography: solvent=acetic acid ester/chlorform 1:1; $R_f$-value 0.110

Analysis: calculated: C 41.62%; H 6.40%; N 24.26%; found: C 41.70%; H 6.40%; N 23.89%

EXAMPLE 2

Production of Formyl-acetic acid ethyl ester-ethoxycarbonylhydrazone (3-Ethoxycarbonylhydrazono-propionic acid ethyl ester)

41.6 g (0.4 mole) hydrazinoformic acid ethyl ester are dissolved in 120 ml ethanol in a three necked 250 ml round flask with stirrer and temperature indicator and 39.2 g (0.4 mole) propiolic acid ethyl ester are added. The temperature rises to 30° C. during the addition and is kept constant for another three hours. After standing over night at room temperature the contents is thickened by evaporation at 40° C. in vacuo. The yellow oily residue crystallizes upon grinding. The crystals are ground with a mixture of 60 ml isopropylether and 60 ml cyclohexane, are sucked off, washed with 100 ml cyclohexane and are dried at room temperature in vacuo to constant weight.

Yield: 71.2 g=88.0 percent of theory
Fp.: 64°–66° C.

Thin layer chromatography:solvent:acetic acid ester/chloroform 1:1; $R_f$-value 0.360

Analysis: Calculated: C 47.52%; H 6.98%; N 13.86%; Found: C 47.21%; H 6.77%; N 14.08%

The products of the process are technically valuable starting materials for the production of biocides, for example 1,2,3-thiadiazole-5-carbonic acid derivatives and of 1,2,3-thiadiazole-5-yl-ureas.

Although certain preferred embodiments of the invention have been disclosed for the purpose of illustration, it will be evident that various changes and modifications may be made without departing from the scope of the invention.

What is claimed is:

1. A process for the production of acylhydrazones of formyl-acetic acid ester of the general formula

wherein $R_1$ is an alkyl group with from 1 to 6 carbon atoms and $R_2$ is an alkoxy group or an amino group comprising contacting a propiolic acid ester of the general formula

with hydrazine derivatives of the general formula

in the presence of a solvent.

2. The process according to claim 1 wherein the alkoxy group has from 1 to 4 carbon atoms.

3. The process according to claim 1 wherein the solvent is a member of the group consisting of water, organic solvents and mixtures thereof.

4. The process according to claim 3 wherein the solvent comprises an alcohol having from 1 to 4 carbon atoms.

5. The process according to claim 3 wherein the solvent is a mixture of water and an alcohol having from 1 to 4 carbon atoms in a weight ratio of from about 2:1 to 1:2.

6. The process according to claim 1 wherein the contacting occurs at temperatures of from about −20° to 100° C.

7. The process according to claim 1 wherein the contacting occurs at temperatures of from about 0° to 50° C.

8. The process according to claim 1 wherein the hydrazine derivative is semicarbazide.

9. The process according to claim 1 wherein the propiolic acid ester is propiolic acid ethyl ester.

10. The process according to claim 1 wherein the hydrazine derivative is hydrazinoformic acid ethyl ester.

* * * * *